United States Patent [19]

Weiss

[11] Patent Number: 6,045,832
[45] Date of Patent: Apr. 4, 2000

[54] USE OF DACEE AND DERIVATIVES FOR TREATING VIRAL DISEASES

[75] Inventor: Ludwig Weiss, Kissing B Augsburg, Germany

[73] Assignee: Ludwig Weiss, Kissing, Germany

[21] Appl. No.: 08/617,820

[22] PCT Filed: Jul. 28, 1994

[86] PCT No.: PCT/EP94/02505

§ 371 Date: Jul. 24, 1996

§ 102(e) Date: Jul. 24, 1996

[87] PCT Pub. No.: WO95/03792

PCT Pub. Date: Feb. 9, 1995

[30] Foreign Application Priority Data

Jul. 29, 1993 [DE] Germany ............................ 43 25 547

[51] Int. Cl.⁷ .................................................. A01N 59/02
[52] U.S. Cl. .......................................... 424/703; 514/665
[58] Field of Search .............................. 424/703; 514/665

[56] References Cited

U.S. PATENT DOCUMENTS

| | | | |
|---|---|---|---|
| 4,378,351 | 3/1983 | Petrovich | 424/164 |
| 4,474,759 | 10/1984 | Petrovich | 424/164 |
| 4,708,965 | 11/1987 | Morgan | 514/563 |

FOREIGN PATENT DOCUMENTS

| | | |
|---|---|---|
| 4619 | 2/1965 | France. |
| WO 90/08540 | 8/1990 | WIPO. |
| WO 94/14473 | 7/1994 | WIPO. |

OTHER PUBLICATIONS

Murphy, F.A., "Virus Taxonomy", pp. 15–57, in Fields Virology, third ed., ed. Fields et al., Lippincott–Raven Publishers, Philadelphia, 1996.

Fenner, F., "Poxviruses", pp. 2673–2702, in Fields Virology, third ed., ed. Fields et al., Lippincott Publishers, Phidelphia 1996.

Flora, et al., "Antioxidant activity and other mechanisms of thiols involved in chemoprevention of mutation and cancer", The American Journal of Medicine, pp. 3C 122–130S Sep. 30, 1991.

Wirth, M.P., "Noveaux medicaments pour le traitment des affections respiratoires", Brevet Special De Medicament, No. 4.619 M, pp. 1–3, Nov. 15, 187.

Roederer et al., "N–acetylcysteine inhibits latent HIV expression in chronically infected cells", AIDs Research and Human Retroviruses, 7/6:563–567,. 1991.

Roederer et al., "N–acetylcysteine: a new approach to anti–HIV therapy", AIDS Research and Human Retroviruses, 8/2:209–217, Feb. 1992.

Beloqui et al., "N–acetyl cysteine enhances the response to interferon–alpha in chronic hetpatitis C: a pilot study", Journal of Interferon Research 13:279–282, 1993.

Droge et al., "Modulation of lymphocyte functions and immune responses by cysteine and cysteine derivatives", The American Journal of Medicine 91, suppl. 3C:140S–144S Sep. 1991.

Database Medline on dialog, No. 06557599, Karg et al., "Glutathione in human melanoma cells. Effects of cysteine, cysteine esters and glutathione isopropyl ester", J. Dermatol. Sci., 1(1):39–45, Jan. 1990.

Translation of French Patent No. 4,619, Novel Medications for the Treatment of Respiratory Disorders, pp. 1–8, Jan. 1967.

Aden et al., 1979, "Cntrolled synthesis of HBsAg in a differentiated human liver carcinoma–derived cell line," Nature 282:615–616.

Roederer et al., 1990, "Cytokine–stimulated human immunodeficiency virus replication is inhibited by N–acetyl–L–cysteine," Proc. natl. Acad. Sci. U.S.A. 84:4884–4888.

Sells et al., 1987, "Production of hepatitis B virus particles in Hep G2 cells transfected with cloned hepatitis B virus DNA," Proc. Natl. Acad. Sci. U.S.A. 84:1005–1009.

Toyoshima et al., 1979, "Disinfectant for hepatitis B virus," Chemical Abstracts 90: Abstract. No. 66875d.

Primary Examiner—Donna C. Wortman
Assistant Examiner—Brenda G. Brumback
Attorney, Agent, or Firm—Pennie & Edmonds LLP

[57] ABSTRACT

The present invention relates to a new use of N,S-diacetylcysteine ethyl ester for the preparation of a pharmaceutical composition for treating virus-induced disease. In particular, the invention concerns the use of DACEE for the preparation of a pharmaceutical composition for treating virus-induced disease, the DACEE used destroying disulfide bridges present in viral proteins.

4 Claims, 4 Drawing Sheets

6,045,832

USE OF DACEE AND DERIVATIVES FOR TREATING VIRAL DISEASES

This is a national phase filing of the Application No. PCT/EP94/02505, which was filed with the Patent Cooperation Treaty on Jul. 28, 1994, and is entitled to priority of the German Patent Application No. P 43 25 547.7, filed Jul. 29, 1993.

I. FIELD OF THE INVENTION

The present invention relates to a new use of thiol compounds for the preparation of a pharmaceutical composition for treating virus-modified diseases. In particular, this invention concerns a use of thiol compounds for the preparation of a pharmaceutical composition for treating virus-induced disease, the thiol compounds used destroying disulfide bridges present in proteins.

II. BACKGROUND OF THE INVENTION

Acute and chronic infections of plants, animals and man, caused by various viral pathogens, represent a serious medical and economic problem. In fact, presumably 60% of the diseases occurring in the industrialized countries are caused by viruses. Thus, diseases caused by hepatitis viruses, for example, are counted among the most frequent infections world-wide. Since said viral infections substantially affect the liver, the progressive destruction of this organ, followed by a subsequent development of a cirrhosis, may finally result in the formation of a hepatocellular carcinoma.

A high specificity degree for the viral pathogen and the simultaneous absence or minimization of health-damaging side-effects have to be regarded as an essential demand to be made on an antiviral therapeutic agent. In this connection, the close linkage of the viral reproductive cycle with the metabolic and replicative functions of the host cell prove to be especially problematic. For the time being, medical research focuses on the development of antiviral agents which impair or prevent the replication of the viral genome, great importance being attached particularly to chemically synthesized nucleoside analogues.

However, one of the main problems of antiviral chemotherapy has to be seen in the fact that no effective substances for therapeutic treatment are available for plurality of significant infective agents such as the hepatitis B virus, for example.

Correspondingly, the present invention is based on the technical problem of providing further therapeutically active and simultaneously pharmaceutically compatible substances for controlling viral diseases.

The solution to this technical is achieved by providing the embodiments characterized in more detail in the claims. In particular, the technical problem is solved in that the present invention discloses the therapeutically active use of thiol compounds for the preparation of a pharmaceutical composition for controlling virus-induced diseases, disulfide bridges present in viral proteins being destroyed by the thiol compounds.

III. SUMMARY OF THE INVENTION

The present invention relates to the new use of thiol compounds for the preparation of a pharmaceutical composition for treating virus-induced disease. In particular, the invention concerns the use of thiol compounds for the preparation of a pharmaceutical composition for treating virus-induced disease, the thiol compounds used destroying disulfide bridges present in viral proteins.

IV. BRIEF DESCRIPTION OF THE DRAWINGS

Figure 3A:
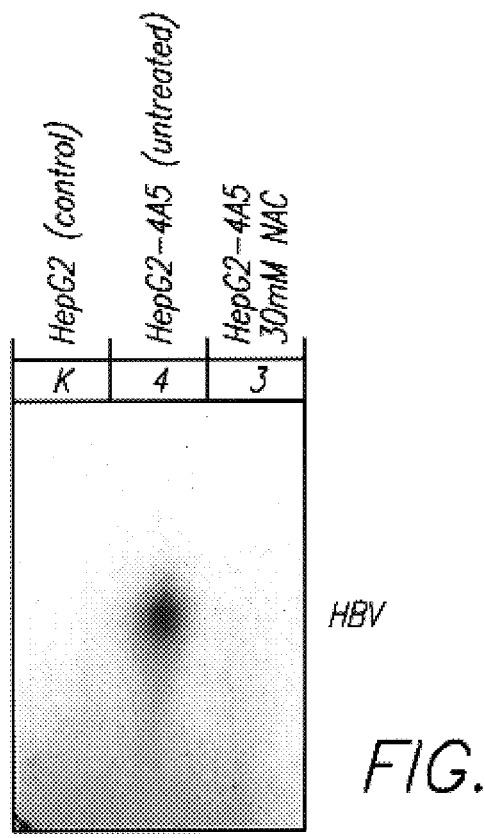

FIG. 3A shows the content of intact HBV viral particles in the cell culture supernatant of HepG2-4A5, the cell line HepG2-4A5 having been incubated additionally with 30 nM NAC concentrations. As a control, the cell supernatant of the cell line HepG2 is shown which does not produce HBV particles (ATCC HB 8065). See, Nature, 1979, 282:615–616.

Figure 3B:
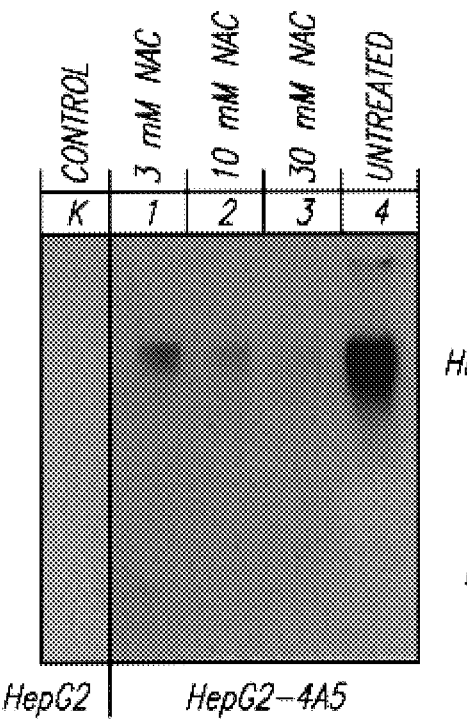

FIG. 3B shows the content of intact HBV viral particles in the cell culture supernatant of HepG2-4A5having been incubated with varying NAC concentrations. As a control the cell supernatant of the cell line HepG2 is shown which does not produce HBV particles (ATCC HB 8065). See, Nature, 1979, 282:615–616, supra.

Figure 4A:
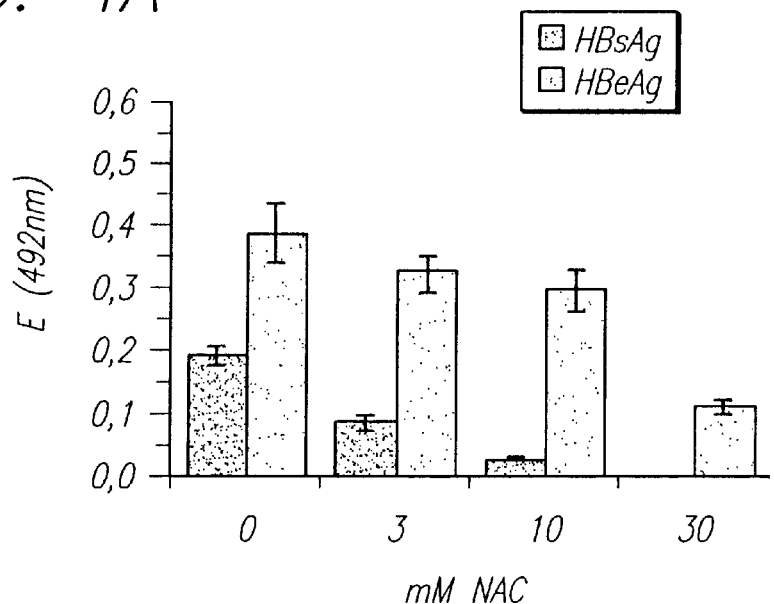

FIG. 4A shows the content of HBsAg and HBeAg in a purchasable HBsAg-positive serum, the serum having been incubated with varying concentrations of NAC.

Figure 4B:
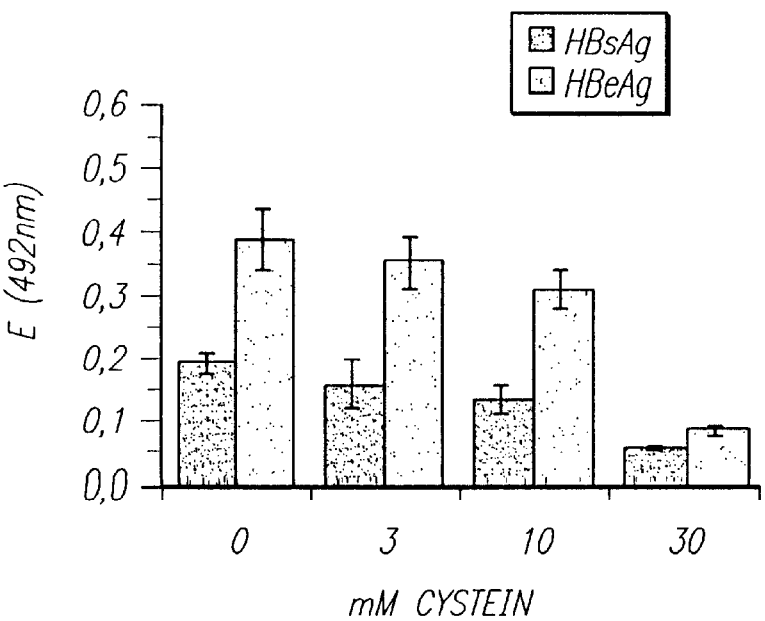

FIG. 4B shows the content of HBsAg and HBeAg in a purchasable HBsAg-positive serum, the serum having been incubated with varying concentrations of cysteine.

Figure 4C:
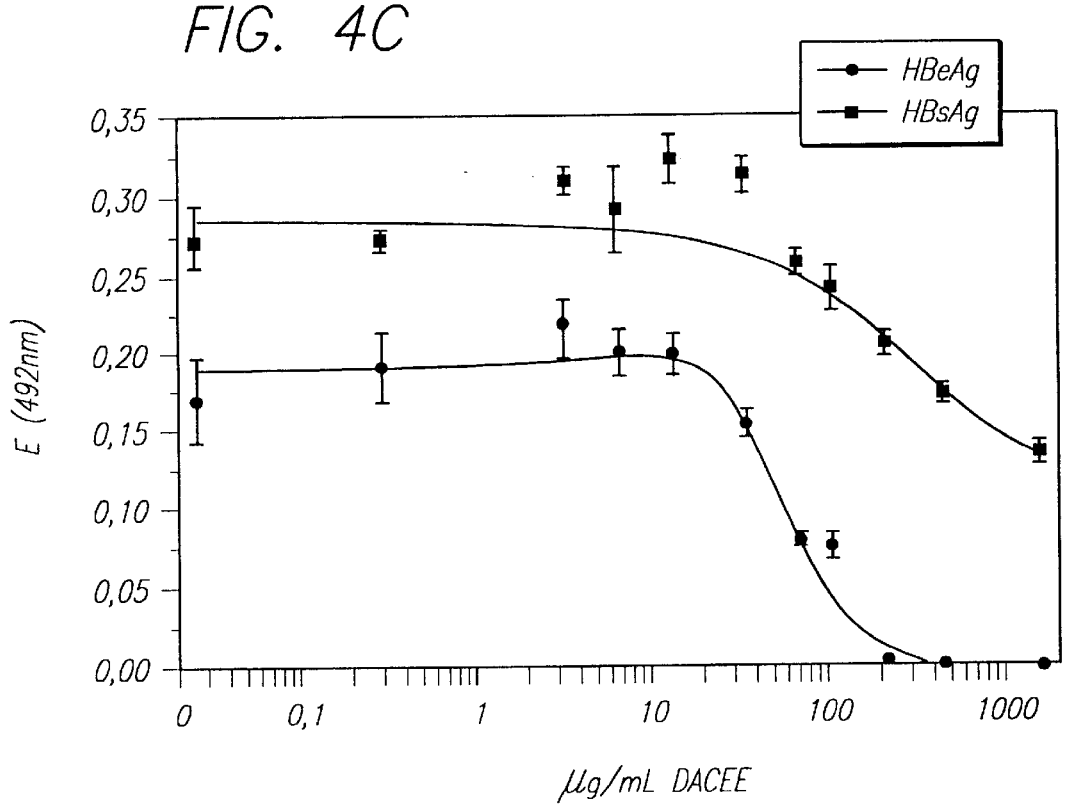

FIG. 4C shows the content of HBsAg and HBeAg in a purchasable HBsAg-positive serum, the serum having been incubated with varying concentrations of DACEE.

Figure 5:
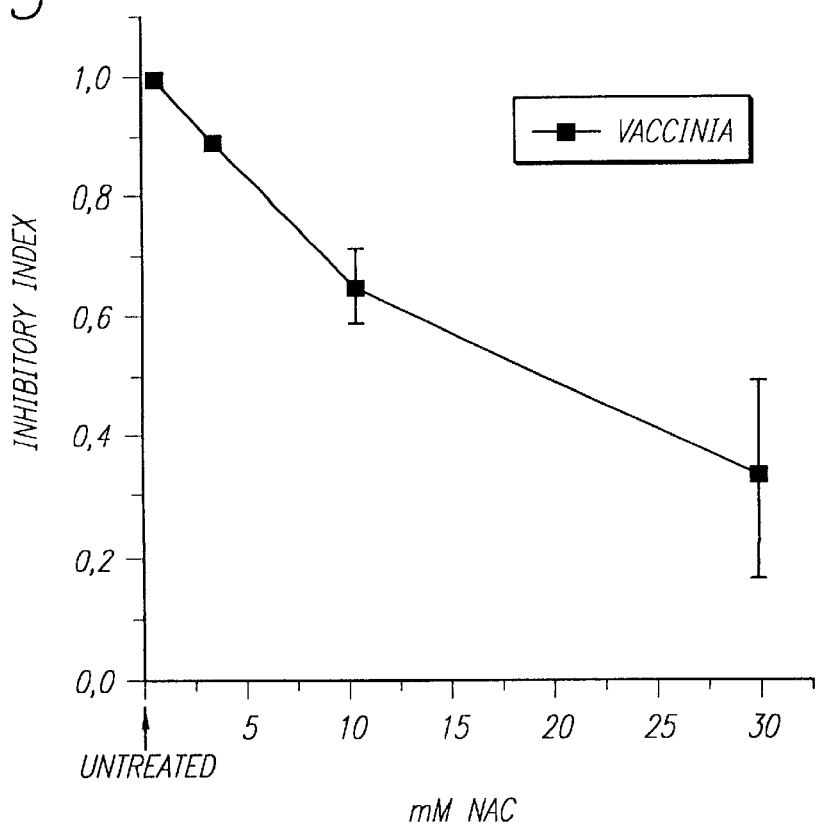

FIG. 5 shows the content of infections vaccinia virus particles, based on the plaque number in the cell culture monolayer of CV1 cells infected with vaccinia virus (ATCC CCL70), the viruses having been preincubated with varying NAC concentrations prior to the infection.

V. DETAILED DESCRIPTION OF THE INVENTION

The expression "thiol compound" is understood to mean chemical compounds which are characterized by the presence of a reduced thiol group (SH group), as well as compounds which in the course of the cellular metabolism can be converted into thiol compounds. Preferred examples of such thiol compounds are cysteine, cysteine derivatives, mercaptoalkanols, such as methanethiol, ethanethiol or mercaptoethanol, dithiocarbamate, thiophenol and 2-mercaptoetthanesulfonic acid. N-acetylcysteine derivatives such as N-acetylhomocysteine, N-acetylcysteine ethyl ester or N,S-diacetylcysteine ethyl ester are examples of cysteine derivatives according to the invention. N-acetylcysteine (NAC) and N,S-diacetylcysteine ethyl ester (DACEE) as well as the derivatives thereof are especially preferred. The thiol compounds used according to the invention are also characterized by their non-toxicity within the concentration range usually used for therapeutic treatments (in the case of NAC: e.g., 600 mg daily over several weeks). In the medical field, NAC is presently used as a mucolytic agent, in the case of paracetamol intoxication and experimentally as HIV and herpes therapeutic agent. Roederer et al., 1990, Proc. Natl. Acad. Sci. U.S.A. 87:4884–4888; U.S. Pat. No. 4 708 965. The thiol compounds according to the invention are characterized particularly by a good compatibility and minor side-effects. Thus, they distinguish themselves particularly from the nucleoside analogues used for the virus therapy up to now.

The expression "virus-induced disease" is understood to mead diseases of the animal and human bodies, which are caused or intensified by viruses. According to the invention they include particularly DNA viruses such as hepadnaviridae, adenoviridae, parvoviridae, papovariridae, adenoviridae, poxviridae, iridoviridae, or RNA viruses, such as picornaviridae, calciviridae, togaviridae, flaviviridae, coronaviridae, rhabdoviridae, filoviridae, paramyxoviridae, orthomyxoviridae, bunyaviridae, arenaviridae, reoviridae, birnaviridae. Within the meaning of this definition herpes viruses and AIDS viruses are not considered to be RNA viruses. preferably to the use of thiol compounds for controlling virus-induced diseases which are caused by hepatitis viruses such as hepatitis A, B, C or delta virus. In particular, the virus-induced disease may be a chronic or acute hepatitis B infection or a hepatocellular carcinoma. Particularly, the expression "virus-induced diseases" is understood to mean diseases which are caused by hepadna viruses such as the hepatitis B virus, the "Woodchuck Hepatitis Virus" (WHV), the "Ground Squirrel Hepatitis Virus" (GSHV), the "Tree Squirrel Hepatitis Virus" (TSHV) or the "Duck Hepatitis Virus" (DHBV), for example. Furthermore, this invention also comprises the use of thiol compounds for controlling vegetable disease which are caused by viral pathogens such as the tobacco mosaic virus (TMV) or the cauliflower mosaic virus (CaMV).

The expression "disulfide bridges present in viral proteins" refers to disulfide bridges which influence the spatial structure and/or the function of viral proteins by intramolecular or intermolecular covalent bonds. Correspondingly, the viral proteins, but at least one viral protein, of the use of thiol compounds according to the invention contain at least one cystein residue. Preferably the viral protein contains several cysteine residues such as HBsAG of the hepatitis B virus, for example. It is well known that disulfide bridges are stabilized by the conformation of the protein, on the other hand. Thus, the amount of thiol compound to be used, which is necessary for the cleavage of the intramolecular or intermolecular disulfide bridges, depends on the accessibility of the respective disulfide bridge(s).

The expression "viral proteins" is understood to mean proteins, preferably coat proteins, such as HBcAG and HBsAG, of a virus. In particular, this expression refers to surface antigens proteins such as HBsAG, for example.

According to the invention, the expression "viral proteins" also include precursor proteins for coat proteins, i.e. proteins which are not present in the final virus.

Furthermore, this invention relates to the use of thiol compounds for the preparation of a pharmaceutical composition for treating virus-induced disease, disulfide bridges present in viral proteins being destroyed by the thiol compound and the thiol compound not influencing the replication of the viral genome.

The following preparations and examples are given to enable those skilled in the art to more clearly understand and to practice the present invention. The present invention is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims. The present invention is explained in more detail by means of the below examples.

VI. EXAMPLES

A. Example 1

Influence Of The Thiol Compounds on the Replication of the Hepatitis B Virus

In order to investigate the influence of thiol compounds on the replication of the hepatitis B virus, use was made of the stably transfected, potentially infectious HBV particle-producing cell lines HepG2 2.2.15 (Sells et al., 1987, *Proc. Natl. Acad. Sci. U.S.A.* 84:1005–1009) and HepG2.4A5 (HepG2 cell line stably transfected with the plasmid pSPT1, 2XHBVneo (cf. Example 4)). NAC, cystein, cystein hydrochloride and DACEE were used as thiol compounds. Cystein was employed s the negative control.

TABLE I shows the HBsAg and HBeAg contents of the cell culture supernatant of the HepG2-4A5 cell line 48 hours after treating the cells with the above compounds. In this connection, the HBsAg content and HBeAg content, respectively, of the untreated cells was arbitrarily set to 1 and the inhibitory index said compounds was determined in relation thereto. Just as in Examples 2 and 3, the antigens were determined by means of a commercially available HbsAg enzyme immunoassay and HBeAg enzyme immunoassay, respectively (Abbott-Laboratories).

The results shown in TABLE I were obtained for NAC also with the cell line HepG2 2.2.15 and, after transient transfection of HepG2 cells (and HuH7 cells, respectively), with the replication-competent HBV plasmid pSPT1, 2xHBV. pSPT1, 2xHBV was pared as described in Example 4.

TABLE I

| SUBSTANCE | CONC. | HBsAg | HBeAg |
|---|---|---|---|
| untreated | | 0.189 ± 0.016 | 0.386 ± 0.048 |
| NAC | 3 mM | 0.085 ± 0.011 | 0.323 ± 0.029 |
| | 10 mM | 0.023 ± 0.002 | 0.295 ± 0.034 |
| | 30 mM | 0.003 ± 0.001 | 0.113 ± 0.0121 |
| cysteine | 3 mM | 0.154 ± 0.039 | 0.348 ± 0.039 |
| | 10 mM | 0.129 ± 0.024 | 0.302 ± 0.029 |
| | 30 mM | 0.053 ± 0.006 | 0.084 ± 0.006 |
| µg/ml DACEE | | | |
| | 0 | 0.241 ± 0.056 | 0.310 ± 0.009 |
| | 0.05 | 0.173 ± 0.034 | 0.281 ± 0.021 |
| | 0.5 | 0.197 ± 0.031 | 0.283 ± 0.004 |
| | 5 | 0.226 ± 0.023 | 0.318 ± 0.009 |
| | 10 | 0.206 ± 0.018 | 0.302 ± 0.026 |
| | 20 | 0.206 ± 0.004 | 0.332 ± 0.019 |
| | 50 | 0.157 ± 0.009 | 0.323 ± 0.013 |
| | 100 | 0.079 ± 0.006 | 0.267 ± 0.007 |
| | 150 | 0.077 ± 0.009 | 0.249 ± 0.013 |
| | 300 | 0.004 ± 0.002 | 0.211 ± 0.007 |
| | 600 | 0.002 ± 0.001 | 0.179 ± 0.004 |
| | 2000 | 0.002 ± 0.001 | 0.139 ± 0.009 |

A marked reduction of HBsAg in the cell culture supernatant could be proved from both NAC-treated cells as well as cysteine- and DACEE-treated cells. A diagram of the above data is depicted in FIGS. 4A, 4B, and 4C. As compared thereto, the control compound cystine showed no influence on the content of the secretable viral antigens, HBsAg and HBeAg (data not shown).

Figure 1:
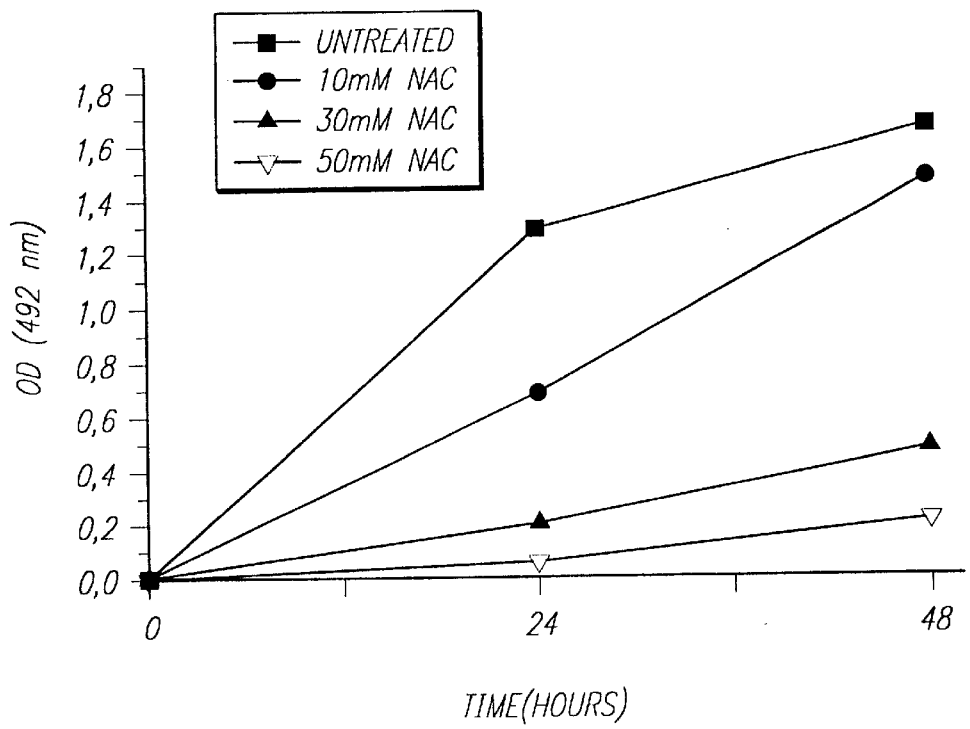
FIG. 1 shows the content, i.e. the amount detected via immunological interaction between viral surface antigen and commercially obtainable antibody, of the viral antigen HBsAG in the cell culture supernatant of HepG2-4A5 cells after treatment with various NAC concentrations as a function of time.
Figure 2:
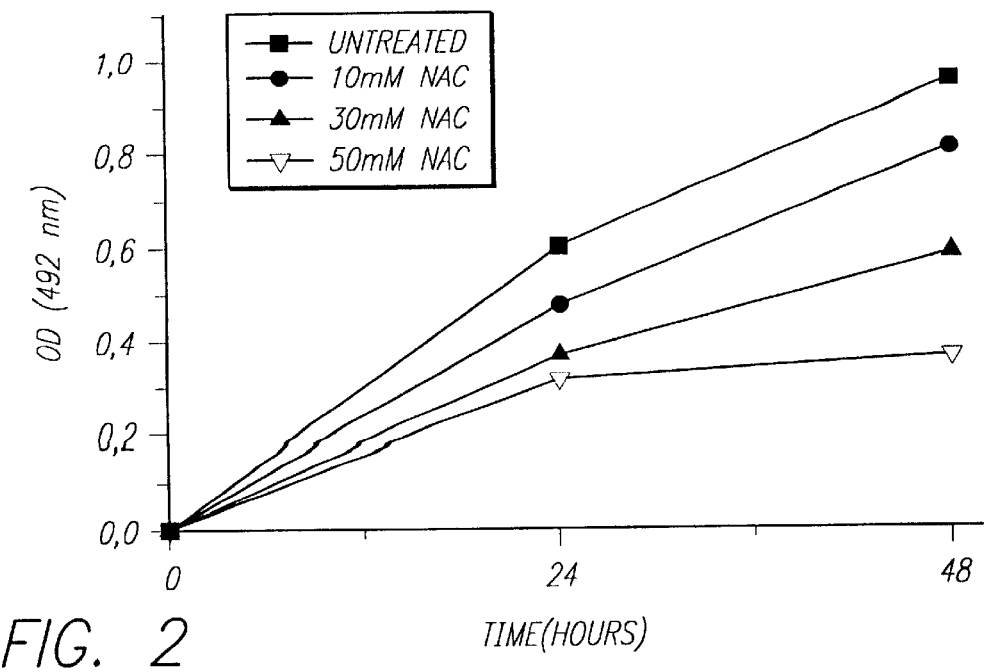
FIG. 2 shows the content of the viral antigen HBeAg in the cell culture supernatant of HepG2-4A5 cells after treatment with various NAC concentrations as a function of time.

Furthermore, the dose-dependent, inhibitory effect of NAC on the content of viral antigens in the cell culture supernatant was investigated by means of the above HBsAg enzyme immunoassay and HBeAg enzyme immunoassay, respectively, as a function of the incubation period (FIGS. 1 and 2). The NAC concentrations used in this connection show no cytotoxic effect on the cells of the cell culture used. The data illustrated in the figure shows a marked dose-dependent inhibitory effect on the content of the investigated viral antigens in the cell culture supernatant.

In order to show that the content of intact and thus potentially infectious viral particles in the cell culture supernatant of the HepG2-4A5 cell line is reduced after treating the cells with thiol compounds, an endogenous-polymerase reaction was carried out. This reaction profits from the fact that the viral polymerase present in the viral capsid can complete in vitro the partially double-stranded HBV genome. By the addition of radioactively labelled nucleotides and subsequent incorporation into the HBV genome it is thus possible to prove the presence of intact, potentially infectious viral particles in a cell culture supernatant. The results shown in FIG. 3A show clearly that the content of potentially infectious intact viral particles in the cell culture supernatant is markedly reduced after treating the cells with NAC.

This result was confirmed in another experiment illustrated in FIG. 3B. For this purpose, the viral particles in the cell culture supernatant of the cell line HepG2-4A5 treated with varying NAC concentrations were specifically enriched by immunoprecipitation with a HBcAg antibody (DAKO GmbH, Hamburg), after removing their outer coat, and then an endogenous-polymer reaction was carried out. Here, too a marked decrease of the hepatitis B virions in the cell culture supernatant occurs after treatment with NAC.

B. Example 2

Investigations Made as to the Mode of Action of NAC, Cysteine and DACEE

In order to investigate whether the antiviral mechanism of action of NAC, cysteine and DACEE, respectively, is based on the destruction of the disulfide bridges present in the viral protein, the cell culture supernatant of the HepG2-4A5 cell line was incubated with the NAC concentrations indicated in TABLE II overnight and then the HBsAg content was determined by means of a purchasable test method (Abbott-Laboratories).

Likewise, purchasable HBsAg-positive serum (Abbott-Laboratories) was preincubated with the NAC, cysteine, DACEE and cysteine hydrochloride concentrations indicated in TABLE III for 5 minutes and then the content of HBsAg and HBeAg was determined by means of the above test method.

TABLES II and III show a marked decrease of HbsAg as a function of the employed concentrations of NAC, DACEE and cysteine hydrochloride, respectively. It can be inferred from the entirety of this data that the antiviral effect of NAC, cysteine, DACEE and cysteine hydrochloride, respectively, is based on a reduction of the disulfide bridges in the HBsAg complex of the hepatitis B virus and thus the build-up of the hepatitis B viral coat is disturbed.

TABLE II

| | HBsAg |
|---|---|
| untreated | 1 |
| 3 mM NAC | 0.95 ± 0.16 |
| 10 mM NAC | 0.54 ± 0.04 |
| 30 mM NAC | 0.22 ± 0.05 |
| 100 mM NAC | 0.03 ± 0.03 |

TABLE III

| SUBSTANCE | CONC. | HBsAg | HBeAg |
|---|---|---|---|
| untreated | | 1.00 ± 0.05 | 1.00 ± 01.07 |
| NAC | 3 mM | 0.79 ± 0.05 | 1.09 ± 0.04 |
| | 10 mM | 0.49 ± 0.03 | 1.17 ± 0.04 |
| | 30 mM | 0.02 ± 0.00 | 1.27 ± 0.09 |
| cysteine | 3 mM | 0.91 ± 0.02 | 1.10 ± 0.06 |
| | 10 mM | 0.68 ± 0.04 | 1.22 ± 0.05 |
| | 30 mM | 0.27 ± 0.05 | 1.21 ± 0.06 |
| DACEE | 0.6 mg/ml | 0.35 ± 0.06 | 1.11 ± 0.04 |
| | 2 mg/ml | 0.06 ± 0.00 | 1.19 ± 0.04 |
| | 6 mg/ml | 0.00 ± 0.00 | 1.09 ± 0.03 |
| cysteine hydrochloride | 3 mM | 0.84 ± 0.004 | 1.17 ± 0.04 |
| | 10 mM | 0.33 ± 0.01 | 1.32 ± 0.05 |
| | 30 mM | 0.11 ± 0.01 | 1.30 ± 0.08 |

C. Example 3

Influence of NAC on the HBsAg Content of the Human Serum of an Acutely Infected Patient In order to investigate whether the in vitro data shown in Example 2 can also be reproduced by means of human serum, the serum sample of an HBV patient in the acute stage of infection was incubated with an increasing amount of NAC. In analogy to the in vitro finding, here, too, a marked decrease of the HBsAg content resulted as a function of the NAC concentration used (TABLE IV).

Since the results shown in TABLE IV were obtained by means of highly infectious human serum which has very high HBsAg and HBeAg titers, the sample was diluted to 1:200 prior to the test so as to remain within the linear range of the HBsAg test used. Preincubation of this representative experiment was 30 minutes.

TABLE IV shows that—as happens after the incubation of the cell culture supernatant with NAC—the HBsAg content is markedly also reduced in the human serum.

TABLE IV

| | HBsAg |
|---|---|
| untreated | 1 |
| 3 mM NAC | 0.27 ± 0.07 |
| 10 mM NAC | 0.12 ± 0.05 |
| 30 mM NAC | 0.04 ± 0.00 |
| 100 mM NAC | 0.00 ± 0.01 |

D. Example 4

Preparation of the pSPT1, 2xHBV and pSPT1, 2xHBVneo Plasmids

For preparing pSPT1, 2xHBV, an HBV portion originating from the plasmid pBRHBadr4 (Fujiama et al., NAR 11, 1983, 4601–4610) was cloned into the cloning vector pSPT19 linearized by BamHI (Boehringer Mannheim, order No.: 909815). Correspondingly, the plasmid pSPT1, 2xHBV contains an HBV genome of full length (BamHI fragment) and additionally a terminal redundance of 621 bp (BamHI/ StuI fragment). Thus, the plasmid pSPT1, 2xHBV contains the minimum portion absolutely necessary to generate all of the viral transcripts, inclusive of the pregonomic RNA having a length of 3.5 kb. This HBV portion is exclusively under the control of autologous promoters.

For the preparation of pSPT1, 2xHBVneo, a neomycin resistance gene which is under the control of the herpes simplex TK promoter was additionally cloned into the vector pSPT1, 2xHBV (meomycin portion of PNEO, Pharmacia, order No.: 27-4924-01). In this case, the cloning strategy was chosen such that the HBV portion and the neomycin resistance portion 3"-3' face each other so as to keep the influence of the TK promoter on the HBV portion as low as possible.

E. Example 5

Influence of NAC on the Replication of the Vaccinia Virus

In order to investigate the influence of thiol compounds, e.g., NAC, on the replication of the vaccinia virus, vaccinia viruses were initially preincubated with 3, 10 and 30 mM, respectively, of NAC for 45 minutes. Then, these viruses were incubated with CV1 cells (generally obtainable monkey kidney cells) for 45 minutes to enable viral adsorption to the cells. Having washed the cells several times, they were covered with softager. After an incubation period of about 48 hours, the non-lyzed cells were dyed by means of crystal violet and the resulting plaques were counted. The plaque number of the untreated control was set to 1.0 and the inhibitory index of the treated cells was determined in relation thereto (cf. TABLE V).

TABLE V discloses that also in the case of the vaccinia virus a reduction of the infectious viral particles is achieved by a thiol compound such as NAC. A diagram of this result is depicted in FIG. 5.

TABLE V

| mM NAC | VACCINA |
|---|---|
| 0 | 1.00 |
| 3 | 0.89 ± 0.01 |
| 10 | 0.64 ± 0.07 |
| 30 | 0.33 ± 0.16 |

All references cited within the body of the instant specification are hereby incorporated by reference in their entirety.

What is claimed is:

1. A method for inhibiting propagation of a hepatitis virus, comprising administering N,S-diacetylcysteine ethyl ester (DACEE) in a pharmaceutically acceptable carrier to a subject infected by a hepatitis virus, in an amount sufficient to effect inhibition of hepatitis virus propagation.

2. The method of claim 1, wherein the virus is a hepatitis B virus.

3. The method of claim 1, wherein the virus is a hepatitis delta virus.

4. A method for inhibiting propagation of a hepadna virus, comprising administering DACEE in a pharmaceutically acceptable carrier to a subject infected by a hepadna virus, in an amount sufficient to effect inhibition of hepadna virus propagation.

* * * * *